United States Patent [19]

Igl

[11] Patent Number: 4,485,819

[45] Date of Patent: Dec. 4, 1984

[54] MECHANICAL ACCESSORY FOR COMMERCIALLY AVAILABLE COMPOUND APPARATUSES FOR ECHO MAMMOGRAPHY

[76] Inventor: Wolfgang Igl, Linprunstrasse 35, 8000 München 2, Fed. Rep. of Germany

[21] Appl. No.: 225,953

[22] Filed: Jan. 19, 1981

[30] Foreign Application Priority Data

Jan. 21, 1980 [DE] Fed. Rep. of Germany ....... 3002067
Nov. 7, 1980 [DE] Fed. Rep. of Germany ....... 3042079

[51] Int. Cl.³ .............................................. A61B 10/00
[52] U.S. Cl. .................................................... 128/660
[58] Field of Search ............................... 128/660–661; 73/618–626

[56] References Cited

U.S. PATENT DOCUMENTS

| | | | |
|---|---|---|---|
| 3,854,471 | 12/1974 | Wild | 128/660 |
| 4,167,180 | 9/1979 | Kossoff | 128/660 |
| 4,206,763 | 6/1980 | Pedersen | 128/660 |
| 4,215,585 | 8/1980 | Kunii et al. | 128/660 X |
| 4,233,988 | 11/1980 | Dick et al. | 73/633 X |
| 4,252,125 | 2/1981 | Iinuma | 128/660 |
| 4,269,066 | 5/1981 | Fischer | 128/660 |
| 4,271,706 | 6/1981 | Ledley | 128/660 X |
| 4,272,991 | 6/1981 | Cribbs | 128/660 X |

Primary Examiner—Kyle L. Howell
Assistant Examiner—Francis J. Jaworski
Attorney, Agent, or Firm—Fleit, Jacobson, Cohn & Price

[57] ABSTRACT

Apparatus for the automatic examination of a patient's breast by echo mammography. A container for holding water has an opening for the receipt of the patient's breast, tyically while the patient is in a prone position. A supporting arm is arranged in the container for movement of an ultrasonic head in a series of essentially semicircular arcs around the breast. A series of sonogram sectional images are produced and are stored in a conventional manner. The opening can be covered with an elastic, diaphragm-like film or a network of strands, permeable to ultrasonic waves, to support the patient's breast in the water bath.

18 Claims, 10 Drawing Figures

MECHANICAL ACCESSORY FOR COMMERCIALLY AVAILABLE COMPOUND APPARATUSES FOR ECHO MAMMOGRAPHY

BACKGROUND OF THE INVENTION

Ultrasonic apparatuses for use with a water bath and foil for examining the female breast are known. The examinations performed with conventional apparatuses using a water bath and foil which is placed on the breast from above the patient in a horizontal position are time-consuming, difficultly reproducible and in addition artifacts occur when foils are used.

The present invention makes it possible to obtain rapid, accurate and reproducible examination results, whilst avoiding the disadvantages of the prior art apparatus.

SUMMARY OF THE INVENTION

The apparatus of this invention permits a substantially completely automatic examination of the female breast, the patient being placed on the apparatus, which is optionally integrated into a couch, in such a way that the breast to be examined is placed through the cover opening, which has rounded edges, and suspended in the water bath. The breast skin surface is surrounded on all sides by water, without any foil being used. The supporting arm, with at least one ultrasonic head arranged in the water beneath the opening, is driven mechanically or electrically and performs a semicircular swinging movement, whose center roughly coincides with the center of the opening plane or is a few centimeters vertically above the center of the opening plane in the inner area of the patient's thorax in order to prevent overlapping of the sound pulses in the image of the breast under examination. In the case of a swinging movement of the supporting arm carrying the ultrasonic head by a maximum of approximately 140° to 180°, a body section is produced in a plane and the sonogram sectional image produced in a known manner is optionally stored on magnetic tape or disk. In order to obtain a plurality of sonogram sectional images, as is required for a complete examination of the breast, following each semicircular vibratory movement of the supporting arm carrying the ultrasonic head the position of the latter with respect to the target organ (breast) can be modified by a minor displacement of the ultrasonic head perpendicularly to the vibration plane of the supporting arm.

Preferably the area of the supporting arm carrying the ultrasonic head is constructed so as to move perpendicularly with respect to the vibration plane of the supporting arm projecting beneath the opening, said movement preferably being telescopic and hydraulic. As a result the patient can lie on the apparatus in a relaxed manner throughout the examination.

The coordination of the vibratory movement of the supporting arm and the hydraulic, telescopic extension of the supporting arm area carrying the ultrasonic head takes place electronically in such a way that after every complete vibratory movement of approximately 140° to 180°, the supporting arm area carrying the ultrasonic head is hydraulically extended by a few millimeters before the arm performs the next vibratory movement of 140° to 180°.

Finally the supporting arm can be constructed so that it is vertically adjustable with respect to the plane of the opening, which ensures that before the start of the examination the optimum distance between the ultrasonic head and the breast can be set.

By means of the apparatus according to the invention series of sonograms sectional images are obtained, which are parallel to one another. In order to fix the exact space coordinates of a single sonogram sectional image the extension position of the supporting arm is recorded simultaneously with the sonogram sectional images. Devices of this type are well known to those skilled in the art and do not form part of the subject matter of the present invention.

According to a preferred embodiment, vertically below the plane of the opening there is a video camera for recording the sound sectional plane during the measurements compared with an experimental finding in the breast area and optionally indicated on the patient's skin by means of a felt tip pen. The vidoe image is recorded simultaneously with the particular sonogram sectional image and is preferably superimposed on the latter.

According to another embodiment, two or more ultrasonic heads, a linear array multielement or a multielement ring transducer are arranged on the supporting arm. If they are arranged in the parallel sound direction, simultaneously a plurality of parallel sonogram sectional images are obtained and recorded, which considerably shortens the examination period. The ultrasonic heads are arranged on the supporting arm in vertically displaced manner with respect to the vibration plane of said arm.

According to another embodiment of the invention a plurality of ultrasonic heads can be arranged in juxtaposed manner on the supporting arm, so that the same section can be obtained with different acoustic frequencies.

Finally the ultrasonic heads are reciprocally arranged at an angle to one another in the sound direction of the supporting arm, which significantly improves the representation and examination of three-dimensional structures.

Whereas in the previously described embodiments parallel sonogram sectional images are obtained, according to another preferred embodiment of the invention a series of sonogram sectional images are obtained rotated with respect to one another about a common axis by the same angular amount.

For this purpose according to an embodiment of the apparatus of the invention the bearing in which the supporting arm is mounted for performing the approximately semicircular vibratory movement about the center of the opening in the water container cover is constructed so as to be at least adjustable in semicircular concentric manner about the opening. Preferably the ultrasonic arm bearings are displaceably constructed on a circular rail running concentrically about the cover opening.

It is particularly advantageous in connection with the latter embodiments that the rotation axis of the sonogram sectional images pass through the nipple, so that in an advantageous manner semicircular sectional images are obtained, which considerably facilitate evaluation and opinion. This also conforms with the anatomical conditions, because all the milk ducts run in star-shaped manner towards the nipples. Consequently it is simpler to represent an extended milk duct in the longitudinal section. Finally this embodiment simplifies the mechanics and consequently the complete apparatus.

DETAILED DESCRIPTION OF THE PREFERRED EMBODIMENT

Figure 1:
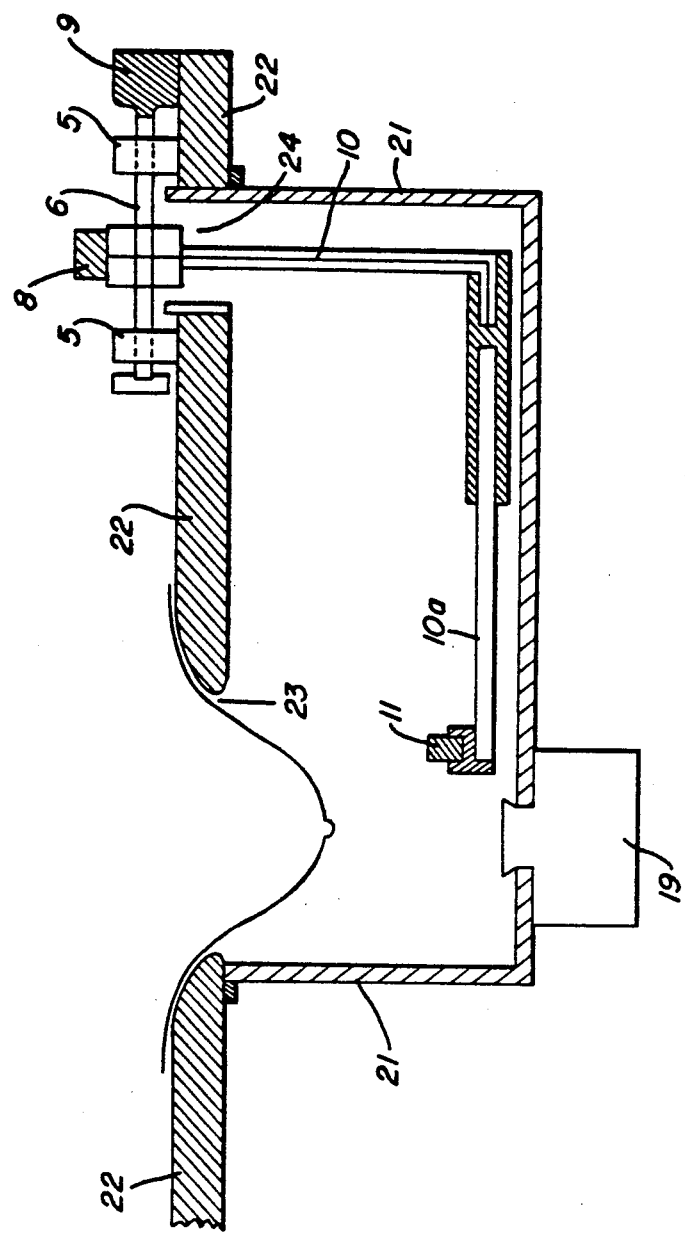
FIG. 1 is a cross-section through a preferred embodiment of the invention.

The apparatus according to FIG. 1 comprises a water container 21, which can be circular or angular. The water container is provided with a cover 22 having an opening 23, through which is placed the patient's breast which is immersed in the water-filled container 21 during the examination. A supporting arm 10 projects into water container 21 through a further opening 24 in cover 22. In the front area 10a located in water container 21 beneath opening 23, there is at least one ultrasonic head 11 directed towards the opening 23. The front area 10a of supporting arm 10 can be hydraulically and telescopically extended and retracted relative thereto. The advance can take place continuously or in predetermined millimeter stages, corresponding at least to the diameter of opening 23. Above opening 24 the edges of the latter carry two bearings 5 in which is pivoted shaft 6, which bridges opening 24. Shaft 6 is substantially rigidly connected to the still free end of supporting arm 10 in the vicinity of opening 24. Thus, on rotating shaft 6 by a given angle, supporting arm 10 with its front portion 10a and the ultrasonic head 11 arranged thereon performs a vibratory or rocking movement by the same angular amount. Shaft 6 is driven by a motor 9 in such a way that the supporting arm portion 10a with ultrasonic head 11 performs an almost semicircular vibratory movement by approximately 140° to 180° within water container 21. During such an almost semicircular vibratory movement of ultrasonic head 11 about the patient's breast hanging through opening 23 a sonogram sectional image is taken and stored. By means of a predetermined advance, e.g. in the range of 1 to 5 mm, a different position of ultrasonic head 11 with respect to the target organ is obtained and a further sonogram sectional image is obtained and recorded which is parallel to the previous image. In this way it is possible to obtain and record a series of parallel sonogram sectional images of the target organ and are immediately or subsequently used for the structural examination thereof.

Preferably supporting arm 10 is connected to shaft 6 in a substantially fixed manner, but adjustable in such a way that the vertical distance from the ultrasonic head 11 to the plane of opening 23 can be adjusted as a function of the size of the breast being examined. This can be brought about, for example, by an electric motor 8, which is also positioned on shaft 6.

The adjustment of the supporting arm area 10a within arm 10 preferably takes place hydraulically, whilst the control system is electronic. On putting into operation ultrasonic head 11 is moved vertically beneath opening 23. In the initial position supporting arm 10 is rotated in such a way by means of shaft 6 that the ultrasonic head almost engages cover 22. The first sonogram sectional image is taken whilst shaft 6, supporting arm 10, supporting arm area 10a with ultrasonic head 11 perform a vibratory movement of approximately 180° until the head 11 once again almost engages cover 22. During the following short interval the predetermined advance (or reverse) of supporting arm portion 10a from supporting arm 10 takes place, followed by the "return swing" of head 11 by once again approximately 180° into its initial position modified by the advance, accompanied by the taking and recording of a second sonogram sectional image parallel to the first image. The time sequence of performing the vibratory movement and the extension or retraction of the supporting arm portion 10a into or out of arm 10 is controlled in a known manner electronically such as by microprocessors. In addition, the taking, recording and storage of the sonogram sectional images take place in a known manner. Synchronously with the recording of the sonogram image a reference recording is made in a known manner of the position of the ultrasonic head 11, so that the correct association of the particular ultrasonic head position to the target organ is ensured.

It is particularly advantageous to use a video camera 19 for recording the position of the ultrasonic head 11 with respect to the target member to be arranged facing opening 23, i.e. on the bottom of container 21. This also ensures the correct matching of the individual sonogram sectional images and the target organ.

Figure 2:
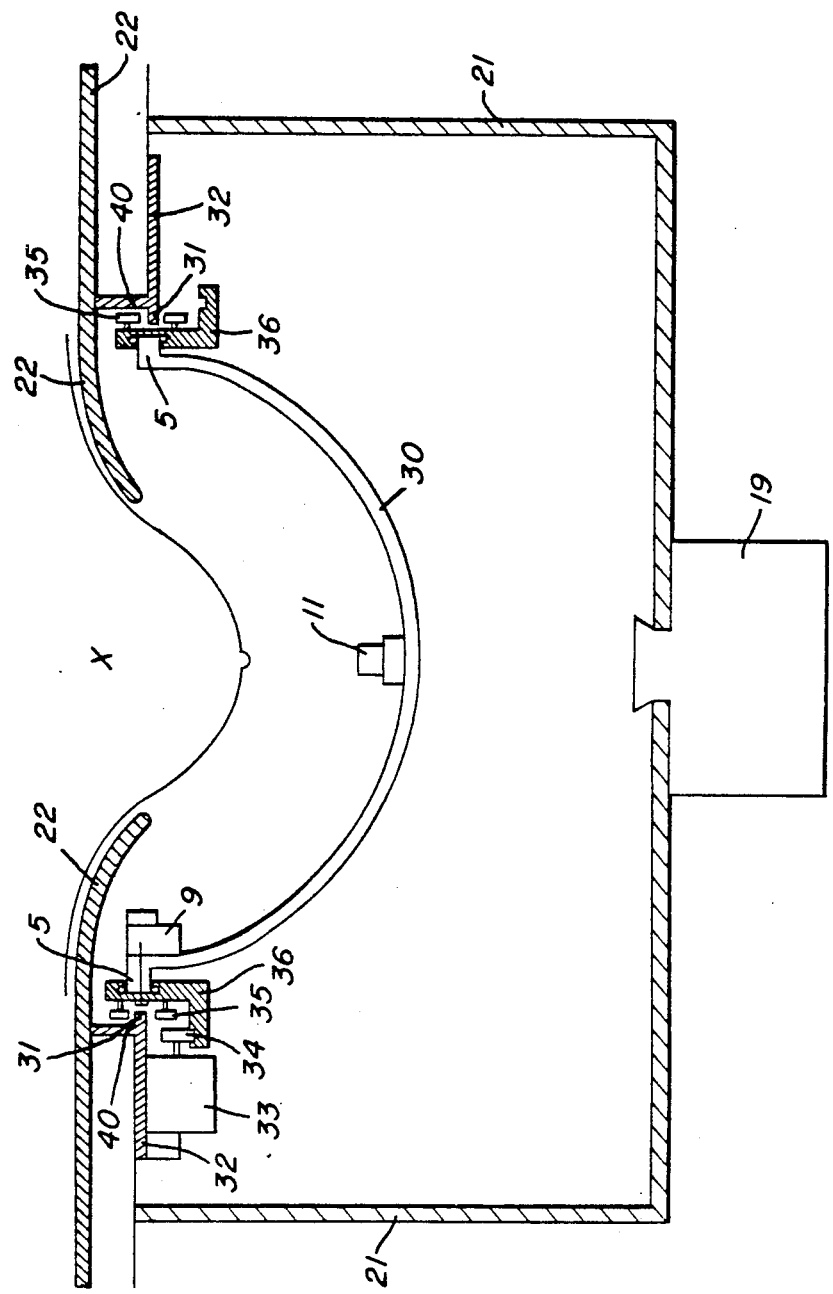
FIG. 2 is a cross-section through another embodiment of the invention.

In the embodiment of FIG. 2 the supporting arm 30 is semicircular and carries the vertically adjustable ultrasonic head 11 in its center. Head 11 is positioned vertically below the center of opening 23. The two free ends of supporting arm 30 are rotatably mounted in bearings 5 by means of motor 9 in the manner described hereinbefore. The essential difference compared with the embodiment described hereinbefore is that the bearings are themselves arranged in a rotary manner in a bearing 40 extending concentrically about opening 23.

This bearing 40 extending in circular and concentric manner about opening 23 can, according to FIG. 2, be an annular component with an inverted T-section fitted to the bottom of cover 22 and arranged concentrically about opening 23. For example the bearings 5 are mounted in rotary and sliding manner by means of rollers 35 on the free end of component 31 projecting into the inner area of the circle.

A motor 33 has a transmission or drive means 34 which includes a gear fitted to the outwardly directed area 32 of the bearing component 40 and is used for driving the semicircular supporting arm 30 with ultrasonic head 11 and bearings 5. For this purpose bearings 5 are arranged in an at least semicircularly constructed component 36 with a cross-sectional L-profile having a radially outwardly directed lower edge constructed for engaging with the transmission or drive means 34.

This construction means that not only can the ultrasonic head 11 perform the previously described movement and produce a sonogram sectional image, but by rotating the semicircular supporting arm 30 with ultrasonic head 11 and bearings 5 in the circular bearing component 40 about the axis perpendicularly through the center of the plane of opening 23, series of sonogram sectional images can be recorded, stored, etc., which, unlike those produced by the apparatus of FIG. 1, are not parallel to one another but are instead reciprocally displaced in their planes by predetermined angular amounts about the axis extending perpendicular through the center of the plane of opening 23.

In operation the supporting arm 30, with the vertically adjustable ultrasonic head 11, passes through the aforementioned angle of approximately 140° to 180°, followed by a predetermined alteration of the angular position of supporting arm 30, etc. with respect to the initial position. Supporting arm 30 once again performs vibratory movements of approximately 140° to 180°, but in this case in the opposite direction. The drive via motors 9 and 31 operate in the manner as described above. The obtaining, recording and storing of the sonogram sectional images and the recording of the relative position of the ultrasonic head 11 with respect to the target object, optionally using once again a video camera 19 placed on the bottom of container 21 facing opening 23, takes place as described above.

Figure 3:
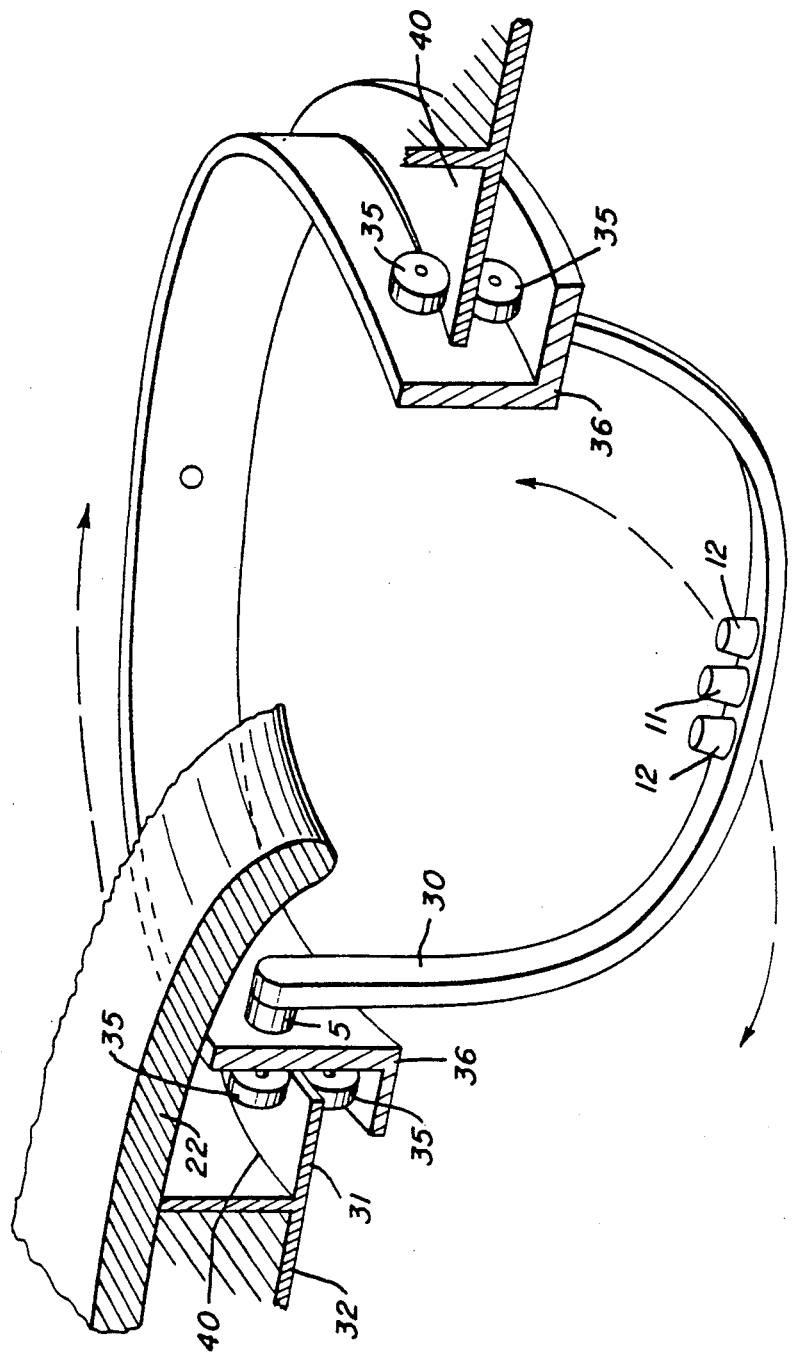
FIG. 3 is an enlarged perspective, cross-sectional view of a portion of the apparatus of FIG. 2.

In FIG. 3 the semicircular component 36 having an L-shaped section is shown. Its outer wall carries a plurality of pairs of rollers 35 by means of which component 36 can rotate on the inwardly directed edge 31 of circular bearing 40. FIG. 3 does not show the drive for the rotary movement of component 36.

Bearings 5 are arranged so as to face one another in the inner wall. Supporting arm 30 with ultrasonic head 11 can be rotated by up to 180° in said bearings. FIG. 3 does not show the drive for the vibratory movement.

Shown in phantom lines are additional ultrasonic heads 12 which may be used in addition to a single head. The presence of more than one head shortens the examination period. A plurality of parallel sonogram sectional images would be recorded.

Figure 4:
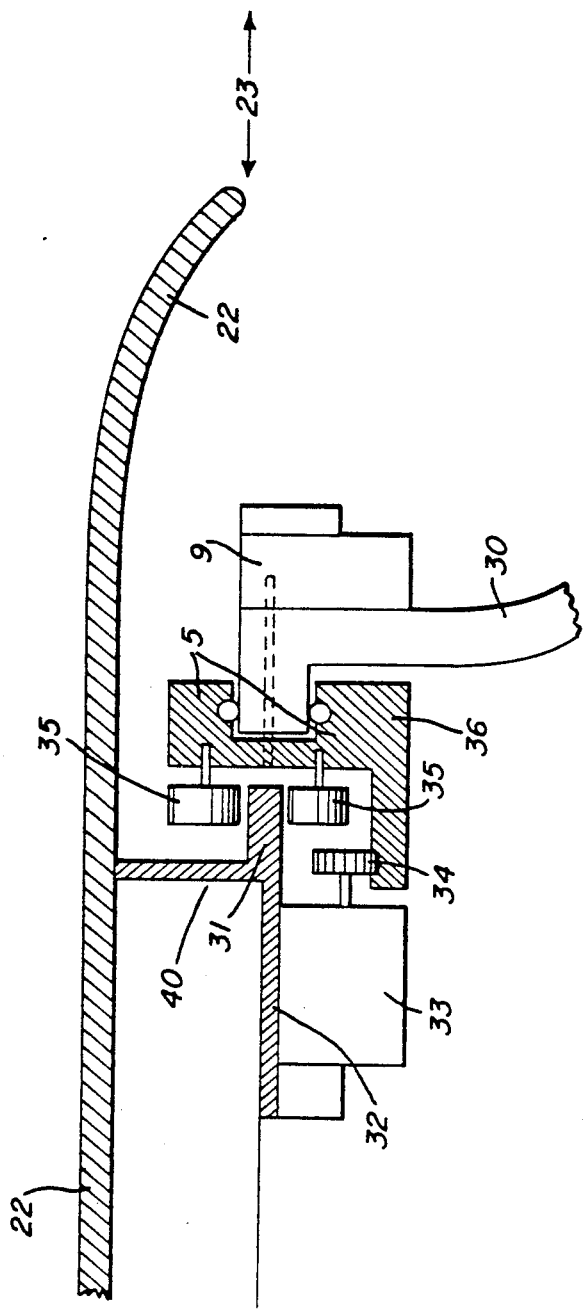
FIG. 4 is an enlarged partial cross-sectional view of the apparatus of FIG. 2.

FIG. 4 shows in cross-section through the area of bearings 5 and 40 of the apparatus according to FIG. 2 the construction for the vibratory movement of the supporting arm 30 and the rotary movement of the circular component 36 with an L-section. For obtaining the vibratory movement of supporting arm 30 an electric motor 9 is provided at the upper end thereof in the vicinity of bearing 5. The rotary drive of the semicircular component 36 in which are arranged the bearings 5 of supporting arm 30 is brought about in annular bearing 40 by means of electric motor 33 arranged on edge 31 projecting into the circle and via a transmission and drive means 34, e.g. a gear. The radially outwardly directed lower edge of component 36 having an L-section is constructed for engaging with the drive means 34.

Figure 5:
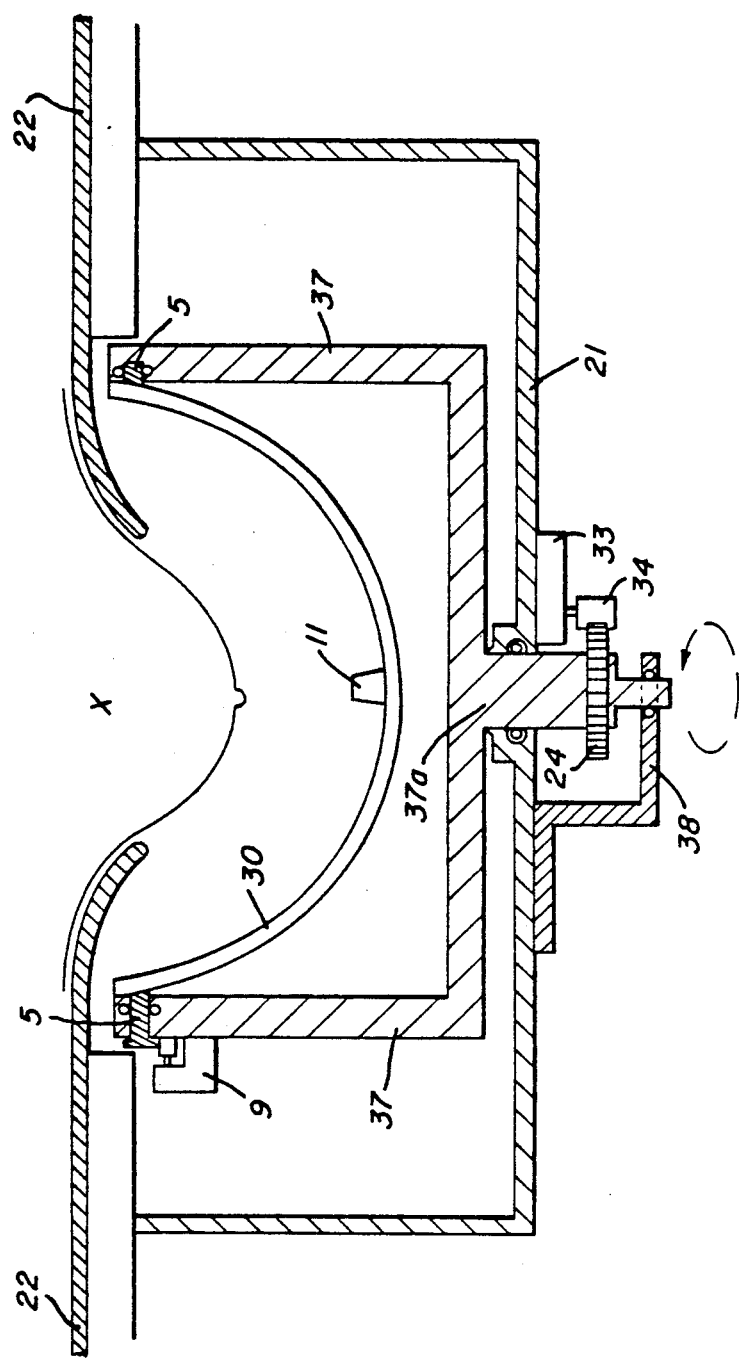
FIG. 5 is a cross-sectional view of another embodiment of the invention.

The embodiment of FIG. 5 is a variant of that of FIG. 2. The vibratory movement of supporting arm 30 in bearings 5 is produced in the indicated manner by drive motor 9. In this embodiment bearings 5 are arranged in a fork-shaped component 37, whose shaft 37a is arranged in rotary and water-tight manner in the bottom of container 21, vertically below the center of the plane of opening 23. The part of area 37a passing through the bottom of container 21 engages with a drive means 34, e.g. a gear driven by motor 33, so that the latter serves to drive the system about the vertical axis. The free end of component 37a is mounted in support 38. The reference numerals otherwise have the same meanings as given hereinbefore.

Figure 6:
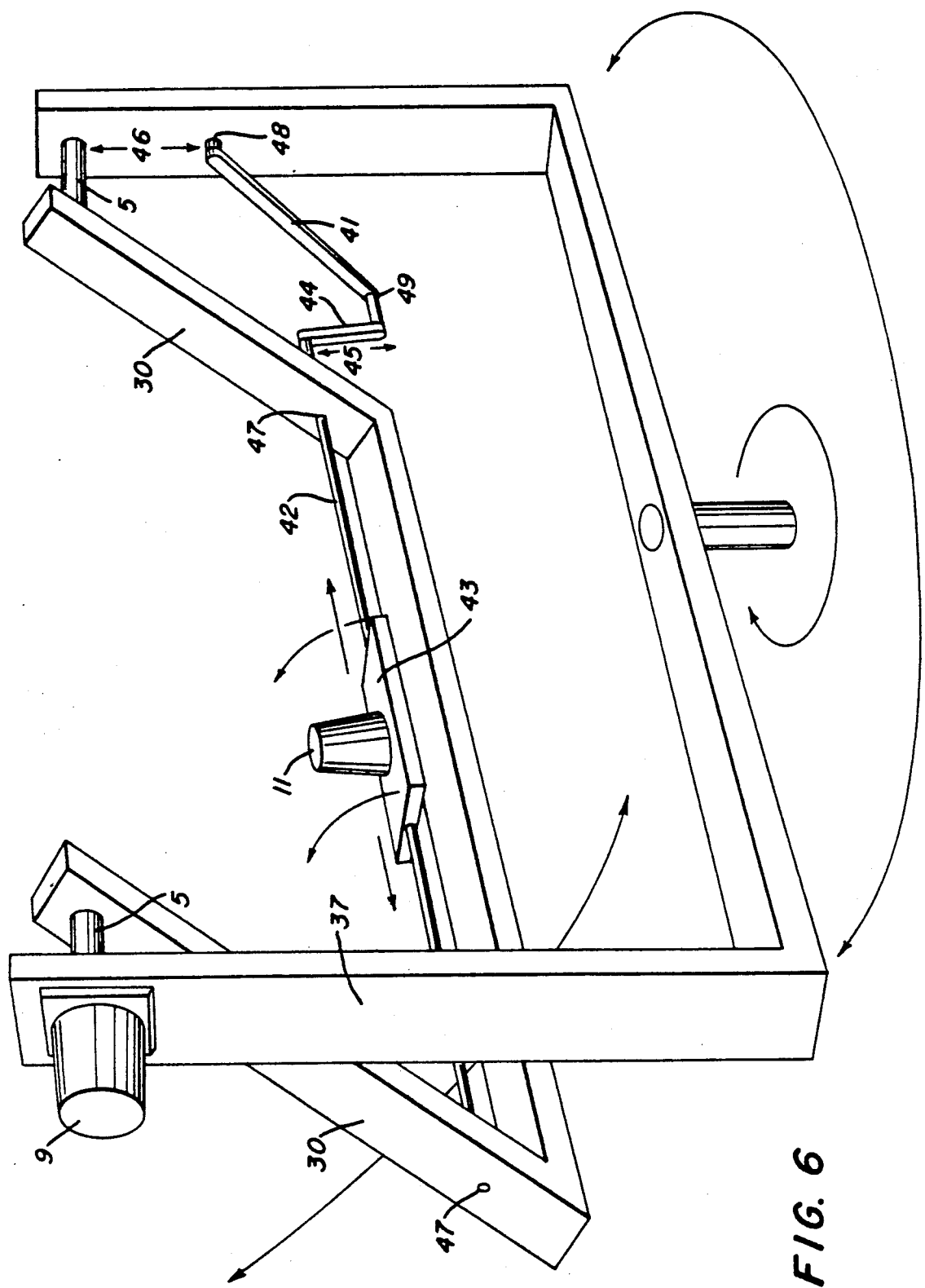
FIG. 6 is an enlarged perspective view of a portion of the apparatus of FIG. 5.

FIG. 6 shows a preferred embodiment of the apparatus according to the invention. This once again forms a further development of the embodiment of FIG. 5 in which ultrasonic head 11 is no longer directly arranged on supporting arm 30. Instead ultrasonic head 11 is fixed to a plate 43 movable to either side of the fork end and positioned on a rod 42 horizontally and rotatably mounted in bearings 47 in the rising areas of supporting arm 30. Rod 42 projects through supporting arm 30 in the vicinity of bearing 47 and is movably connected to the next rising arm of the fork-shaped component 37 in bearing 48 via a crank-shaped or parallelogram-like lever system 44, 41. Rod 41 is movably fitted in the bearing at point 48 and 49.

Ultrasonic head 11 is rotated about a different rotation axis compared with the supporting arm 30. The hinged lever connection between rod 42 and the rising area of the fork-shaped component 37 can comprise, for example, a hinged member 44 which is vertically aligned in the inoperative position, which is rigidly connected to rod 42 and forms an angle of 90° with the latter. At the other end of member 44 is pivoted a rod, which is parallel to rod 42. The free end of said rod is, for example, connected by means of a ball and socket joint 49 to the other member 41 of the hinged member, whose free end is connected by means of a ball and socket joint 48 with the next rising area of the fork-shaped component 37. The vertical spacing 46 from this connection point to the bearing 5 and the length of member 44 (with a corresponding length matching of member 41) determines the extent by which the rotation angle of ultrasonic head 11 differs from that of supporting arm 30.

When using this apparatus the intersection of all sound waves from the ultrasonic head 11 no longer necessarily occurs on the rotation axis of supporting arm 30, as is the case e.g. with the embodiment of FIG. 5, but can instead be varied by corresponding changes to the spacing 46 and the length of member 44.

Figure 8:
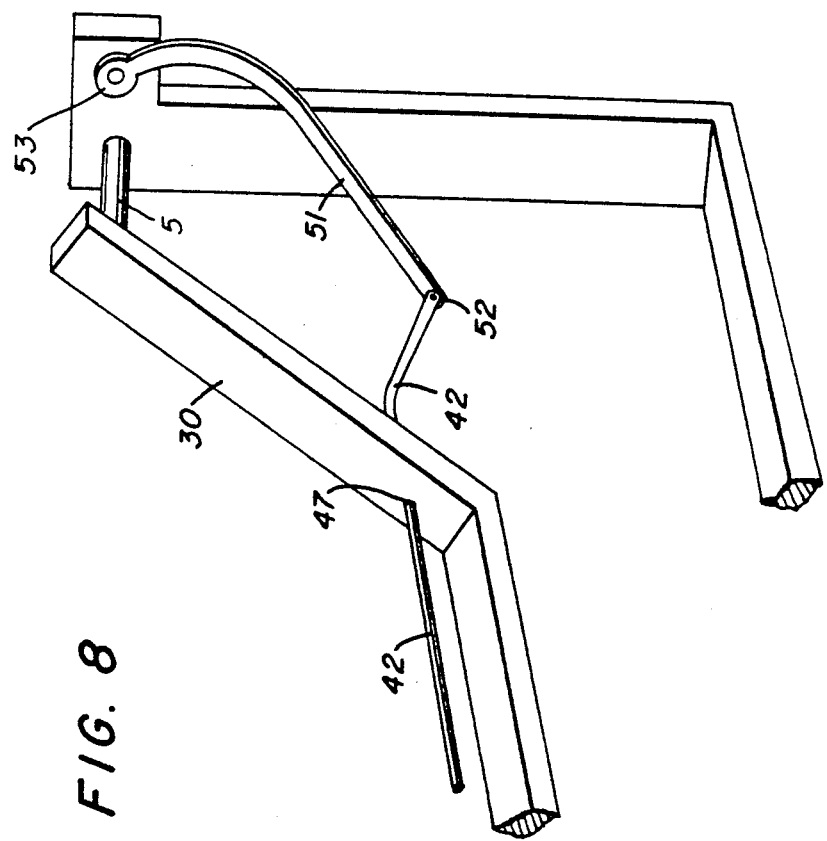
FIG. 8 is an alternative configuration of the apparatus of FIG. 6.

In a further development of the embodiment of FIG. 6 shown at FIG. 8, the bearing 53 (corresponding to bearing 48 in FIG. 6) is disposed in the rising arm of the fork-shaped component 37 adjacent to bearing 5. Rod 51 (corresponding to rod 41 in FIG. 6) is curved and is connected by means of a ball and socket joint 52 with the extension of rod 42, the extension being bent away from the main direction of rod 42 in an angle of about 90°.

Figure 7:
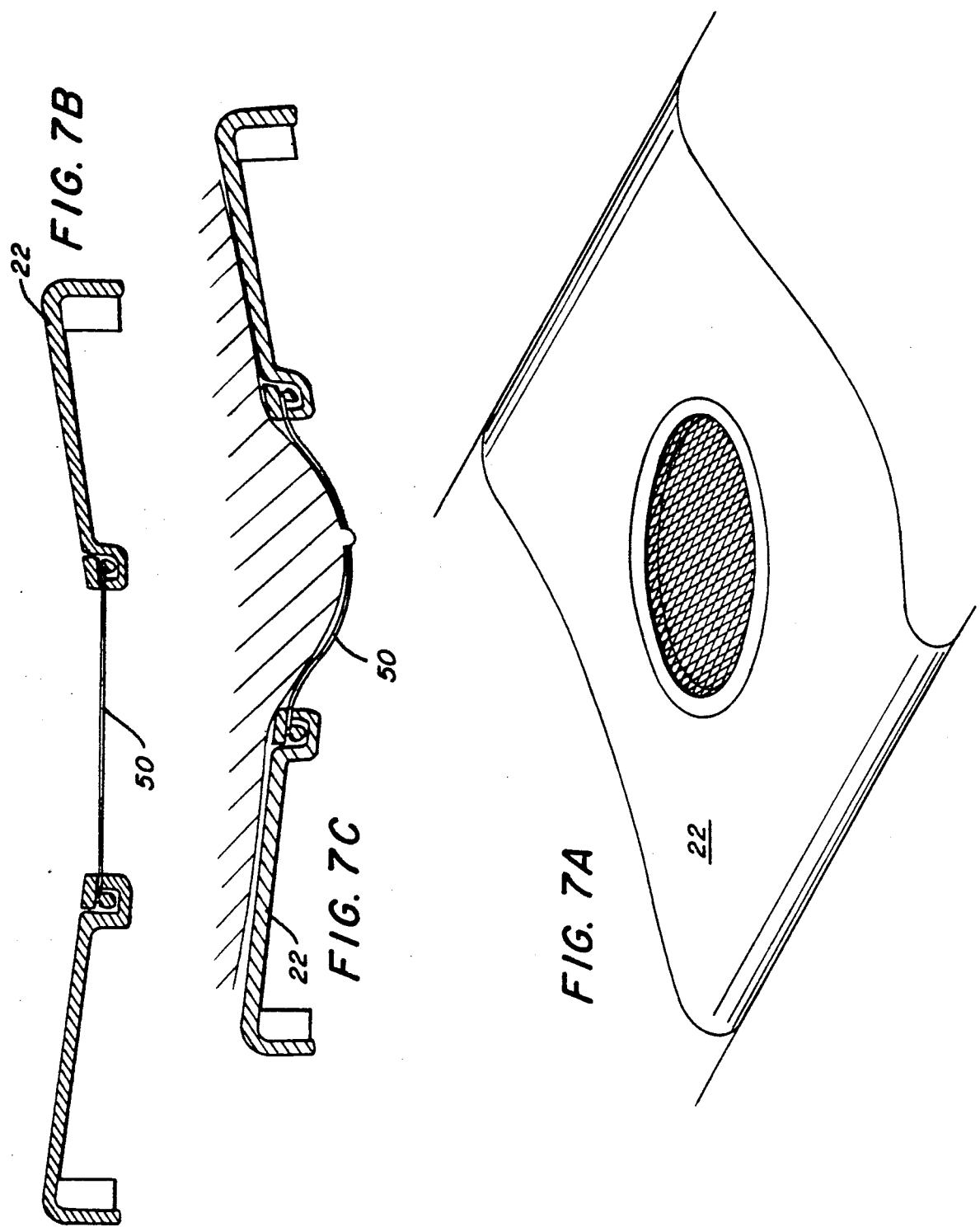
FIG. 7A is a perspective view of a cover with a network covering the opening.
FIG. 7B is a cross-sectional view of the cover of FIG. 7A.
FIG. 7C shows the cover of FIG. 7B in use.

FIGS. 7A and 7B show cover 22 in which the opening is provided with a foil or preferably a network 50. If a foil is used for attaching to the skin of the breast an oil or a commercial contact gel must be applied between foil and skin. If preferably a thin elastic and easily replaceable network made from very fine plastic threads which do not disturb the ultrasonic pulse is stretched over the opening. As shown in FIG. 7C the breast is held in a slightly compressed immovable manner, instead of hanging freely and movably into the water bath. This prevents movement artifacts during echo mammography, whilst simultaneously reducing the thickness of the tissue to be penetrated by the ultrasonic waves. This permits the use of the ultrasonic heads of higher than normally used frequencies, which permit a better diagnosis of breast cancer.

What is claimed is:

1. Mechanical accessory apparatus for a device conducting echomammography for ultrasonic examination of the female breast, said apparatus comprising:
    a water container with at least one aperture in a cover of the container, said cover generally occupying a plane and adapted for opposition with the chest;
    a supporting arm projecting into said water container below said aperture;
    at least one ultrasonic head carried by said supporting arm and directed towards the aperature; and
    a rotary means for rotating said supporting arm in a semi-circular movement around an axis situated in the plane of said cover, said axis extending through a center point of the aperture for maintaining a constant distance, during rotation of said supporting arm, between said ultrasonic head and the breast to be examined.

2. Apparatus according to claim 1 further comprising a diaphragm-like supporting means substantially covering said aperture which can easily be penetrated by ultrasonic waves.

3. Apparatus according to claim 2 wherein said diaphragm-like support means is a network of strands for supporting the breast.

4. Apparatus according to claim 2 wherein said diaphragm-like support means is a thin, elastic foil for supporting the breast.

5. Apparatus according to claim 1 wherein the supporting arm includes a supporting arm area for carrying the ultrasonic head, said area constructed so as to move vertically with respect to the surface of rotation of the supporting arm projecting beneath the opening.

6. Apparatus according to either claims 1 or 2 wherein the supporting arm area carrying the ultrasonic head is constructed so as to be hydraulically and telescopically extendable from the supporting arm in a direction perpendicular to its surface of rotation, defined by the supporting arm.

7. Apparatus according to either claims 1 or 2 wherein the supporting arm is constructed so as to be vertically adjustable at right angles to the plane of the aperture.

8. Apparatus according to claim 1 wherein two or more ultrasonic heads are arranged on said supporting arm.

9. Apparatus according to claim 8 wherein said two or more ultrasonic heads are at least one of the same and different frequencies and arranged at a angle from one another in the sound direction.

10. Apparatus according to claim 1 wherein said plurality of ultrasonic heads of different frequencies are arranged in a parallel sound direction.

11. Apparatus according to claim 1 further comprising a camera for recording the position of the said at least one ultrasonic head, the camera arranged vertically below the plane of the opening during the measurement.

12. Apparatus according to claim 1 wherein the supporting arm includes a bearing constructed to be adjustable around the perimeter of the aperture.

13. Apparatus according to claim 12 wherein the bearing is displaceably constructed in an annular rail arranged concentrically about the aperture and below the cover.

14. Apparatus according to claim 12 wherein the bearings of the supporting arm are within a fork-shaped component, a portion of the fork-shaped component being passed in rotary and water-tight manner through the bottom of the container.

15. Apparatus according to claim 14 wherein the rotation axis of the fork-shaped component portion is coaxial with a central axis through the opening.

16. Apparatus according to claim 1 wherein the cover with the opening is constructed as a couch for the patient arranged over the water container.

17. A mechanical accessory apparatus for compound devices for echomammography by ultrasonic examination of the female breast, said apparatus comprising:
    a water container with a cover having at least one aperture with rounded edges;
    at least one of a semi-circular and U-shaped supporting arms projecting into the container beneath said aperture for performing approximately semi-circular vibrating movements around an axis situated in the plane of the cover and extending through the center of said aperture;
    a fork-shaped component pivotably supporting said supporting arm;
    at least one ultrasonic head carried by said supporting arm and directed at the aperture;
    a shaft portion of said fork-shaped component supported by the bottom of the container adapted for rotation of said fork-shaped component;
    a plate fixed to a rotary rod passing through said supporting arm and said ultrasonic head arranged on said plate;
    a lever system interconnected by a plurality of hinge joints connecting one of said rotary rod to a rising member of said fork-shaped component for rotation of said supporting arm.

18. Mechanical accessory apparatus for a device conducting echomammography for ultrasonic examination of the female breast, said apparatus comprising:
    a water container with at least one aperture in a cover of the container;
    a supporting arm projecting into said water container below said aperture;
    a bearing on said supporting arm concentric with said aperture for adjustment of said supporting arm about said aperture; and
    a rotating means for rotating said supporting arm in a semi-circular movement around an axis situated in the plane of said cover, said axis extending through a center point of the aperture for maintaining a constant vertical distance, during rotation of said supporting arm, between said ultrasonic head and the breast to be examined.

* * * * *